US006849185B1

United States Patent
Wu et al.

(10) Patent No.: US 6,849,185 B1
(45) Date of Patent: Feb. 1, 2005

(54) CHARGED MEMBRANE

(76) Inventors: Xiaosong Wu, 1210 Stonebridge Rd., Pensacola, FL (US) 32514; Joe L. Kinsey, Jr., 9776 Beverly Rd., Irvington, AL (US) 36544-0934; Michael Ishee, 5630 Leesway Blvd., Pensacola, FL (US) 32504; Peter Konstantin, 4952 Carter Ct., Boulder, CO (US) 80301; Joel Shertok, 117 Drummond Farms La., Newark, DE (US) 19711-8323; Yujing Yang, 14 Pulsifer St., Newton, MA (US) 02460

( * ) Notice: Subject to any disclaimer, the term of this patent is extended or adjusted under 35 U.S.C. 154(b) by 0 days.

(21) Appl. No.: 09/959,882

(22) PCT Filed: May 12, 2000

(86) PCT No.: PCT/US00/12894
§ 371 (c)(1),
(2), (4) Date: Jan. 29, 2002

(87) PCT Pub. No.: WO00/69549
PCT Pub. Date: Nov. 3, 2000

Related U.S. Application Data

(60) Provisional application No. 60/134,197, filed on May 14, 1997.

(51) Int. Cl.[7] .................................................. B01D 69/12

(52) U.S. Cl. .................. 210/660; 210/488; 210/490; 210/500.24; 210/500.27; 210/500.41; 210/502.1; 210/504; 264/41; 427/244; 427/245; 427/487; 436/178; 521/27

(58) Field of Search ................................. 210/435, 488, 210/490, 500.21, 500.24, 500.27, 500.36, 500.41, 502.1, 504, 650, 651, 653, 660, 767; 264/41; 427/244, 245, 487; 436/177, 178; 521/27

(56) References Cited

U.S. PATENT DOCUMENTS

| 4,380,590 A | | 4/1983 | Chong |
| 4,523,995 A | | 6/1985 | Pall et al. |
| 4,618,533 A | * | 10/1986 | Steuck ................... 428/315.7 |
| 4,702,840 A | | 10/1987 | Degen et al. |
| 4,980,067 A | | 12/1990 | Hou et al. |
| 5,004,543 A | | 4/1991 | Pluskal et al. |
| 5,021,160 A | | 6/1991 | Wolpert |
| 5,032,281 A | | 7/1991 | Nagamatsu et al. |
| 5,051,114 A | | 9/1991 | Nemser et al. |
| 5,085,780 A | | 2/1992 | Ostreicher |

(List continued on next page.)

FOREIGN PATENT DOCUMENTS

| EP | 0 228 072 B1 | 7/1987 |
| EP | 0 347 755 B1 | 12/1989 |
| WO | WO 98/01208 | 1/1998 |

OTHER PUBLICATIONS

Anspach, F. et al., J. Chrom. A., 711, 81–92 (1995).

(List continued on next page.)

Primary Examiner—John Kim
(74) Attorney, Agent, or Firm—Leydig, Voit & Mayer, Ltd.

(57) ABSTRACT

The present invention provides a hydrophilic charged microporous membrane comprising a porous hydrophobic substrate and a coating comprising a charge-providing agent. The present invention further provides a hydrophilic charged membrane comprising a porous hydrophobic substrate and a hydrophilic charge-providing agent distributed within the substrate. The present invention further provides a filter as well as a filter device comprising the inventive hydrophilic charged membrane. The present invention further provides a process for treating a fluid containing bacterial contaminants such as endotoxins comprising contacting the membrane with the fluid to provide a bacterial contaminant depleted fluid.

24 Claims, 7 Drawing Sheets

U.S. PATENT DOCUMENTS

| | | |
|---|---|---|
| 5,116,650 A | 5/1992 | Browser |
| 5,128,041 A | 7/1992 | Degen et al. |
| 5,151,189 A | 9/1992 | Hu et al. |
| 5,269,931 A | 12/1993 | Hu et al. |
| 5,277,812 A | 1/1994 | Hu et al. |
| 5,407,581 A * | 4/1995 | Onodera et al. ............ 210/654 |
| 5,438,128 A | 8/1995 | Nieuwkerk et al. |
| 5,462,867 A | 10/1995 | Azad et al. |
| 5,531,893 A | 7/1996 | Hu et al. |
| 5,543,054 A | 8/1996 | Charkoudian et al. |
| 5,749,942 A | 5/1998 | Mattis et al. |
| 6,183,640 B1 | 2/2001 | Wang |
| 6,258,272 B1 | 7/2001 | Wang et al. |

OTHER PUBLICATIONS

Ball P.R. et al., *Endotoxin Retention Capabilities of the Pall Intravenous Set Saver*, BM2117 (1990).

Baumgartner, T. et al., Amer. J. Hosp. Pharm., 43, 681–684 (1986).

Belanich, M. et al., Pharm. Tech., 142–150 (1996).

Held, D. et al., Pharm. Tech., 32–38 (1997).

Horibe, K. et al., J. Par. Ent. Nutr., 14(1), 56–59 (1990).

Hou, K. et al., Biochem. Biophys. Acta, 1073, 149–154 (1991).

Hou, K. et al., Biotech. Appl. Biochem., 12, 315–324 (1990).

Kendall, K., et al., *"Endotoxin Rentention Capabilities of Positively Charged Nylon and Positively Charged Polysulphone Membrane Intravenous Filters"*, Pall Technical Report, (1994).

Petsch D. et al., J. Chrom. B., 693, 79–91 (1997).

Richards, C. et al., J. Clin. Pharm. Ther., 19, 199–202 (1994).

Spielberg, R. et al., *Labortory Evaluation of Endotoxin Retention By Pall 0.2μm Posidyne Membrane*, 1–ER–96, (1991).

* cited by examiner

CHARGED MEMBRANE

This application is a 35 USC 371 of PCT/US00/12894 which was filed on May 12, 2000 and was published in the English language. This application claims the benefit of U.S. provisional patent application 60/134,197, filed May 14, 1999, which is incorporated by reference.

TECHNICAL FIELD OF THE INVENTION

The present invention generally relates to hydrophilic charged membranes. These membranes find use in the separation, removal, or reduction of bacterial contaminants such as endotoxins from water, saline solutions, and other fluids.

BACKGROUND OF THE INVENTION

The removal of bacterial contaminants such as endotoxins from fluids, such as pharmaceutical products, has been a challenge to the separation industry. Attempts have been made to meet the challenge by using charge modified membranes.

The bacterial contaminant removal efficiency of some of these membranes is limited, e.g., the binding capacity for contaminants has been low. Thus, these membranes have reduced endotoxin retention characteristics. Such characteristics lead to early breakthrough of endotoxins into the filtered fluid. Further, some of the membranes have low water flow rates. Some of these membranes have limited water and/or saline wettability.

Accordingly, there exists a need for a membrane that has improved bacterial contaminant, particularly endotoxin, retention characteristics. There further exists a need for a membrane that has water and/or saline solution wettability and water permeability. The present invention provides for ameliorating at least some of the disadvantages of the prior art. These and other advantages of the present invention will be apparent from the description as set forth below.

BRIEF SUMMARY OF THE INVENTION

Many of the foregoing needs have been fulfilled by the present invention, which provides, in one embodiment, a hydrophilic charged microporous membrane comprising a porous hydrophobic substrate and a coating comprising a charge-providing agent. The charge-providing agent can be positively charged or negatively charged. The present invention further provides a process for preparing the hydrophilic charged membrane comprising contacting the porous hydrophobic substrate with a composition comprising a charge-providing agent or a precursor thereof.

The present invention further provides, in another embodiment, a hydrophilic charged membrane comprising a porous hydrophobic matrix and a charge-providing agent distributed within the hydrophobic matrix. The charge-providing agent can be positively charged or negatively charged. The present invention further provides a process for preparing the above membrane comprising forming the membrane from a solution comprising a hydrophobic polymer capable of forming a porous hydrophobic matrix, a solvent for the hydrophobic polymer, a pore former, and a charge-providing agent or a precursor thereof. The formation of the membrane can involve phase inversion.

The present invention further provides a filter device comprising the inventive hydrophilic charged membranes. The present invention further provides a process for treating a fluid containing bacterial contaminants, e.g., endotoxins, the process comprising placing the fluid in contact with a hydrophilic charged membrane and recovering a bacterial contaminant-depleted fluid. If desired, the bacterial contaminant-depleted fluid can be returned or administered to a patient. The term "bacterial contaminants" herein refers to endotoxin contaminants that result or originate from bacteria including lipopolysaccharides and lipoteichoic acid.

While the invention has been described and disclosed below in connection with certain embodiments and procedures, it is not intended to limit the invention to those specific embodiments. Rather it is intended to cover all such alternative embodiments and modifications as fall within the spirit and scope of the invention.

BRIEF DESCRIPTION OF THE DRAWINGS

FIG. 1 depicts the endotoxin reduction achieved when a saline solution containing an endotoxin challenge contamination was filtered using the membrane embodiment described in Example 2.

FIG. 2 depicts the endotoxin reduction achieved when water containing an endotoxin challenge contamination was filtered using the membrane embodiment described in Example 2.

FIG. 3 depicts the endotoxin reduction achieved when a saline solution containing an endotoxin challenge contamination was filtered using the membrane embodiment described in Example 4.

FIG. 4 depicts the endotoxin reduction achieved when water containing an endotoxin challenge contamination was filtered using the membrane embodiment described in Example 4.

FIG. 5 depicts the endotoxin reduction achieved when a saline solution containing an endotoxin challenge contamination was filtered using the membrane embodiment described in Example 5.

FIG. 6 depicts the endotoxin reduction achieved when a saline solution containing an endotoxin challenge contamination was filtered using the membrane embodiment described in Example 6.

DETAILED DESCRIPTION OF THE INVENTION

Figure 1:
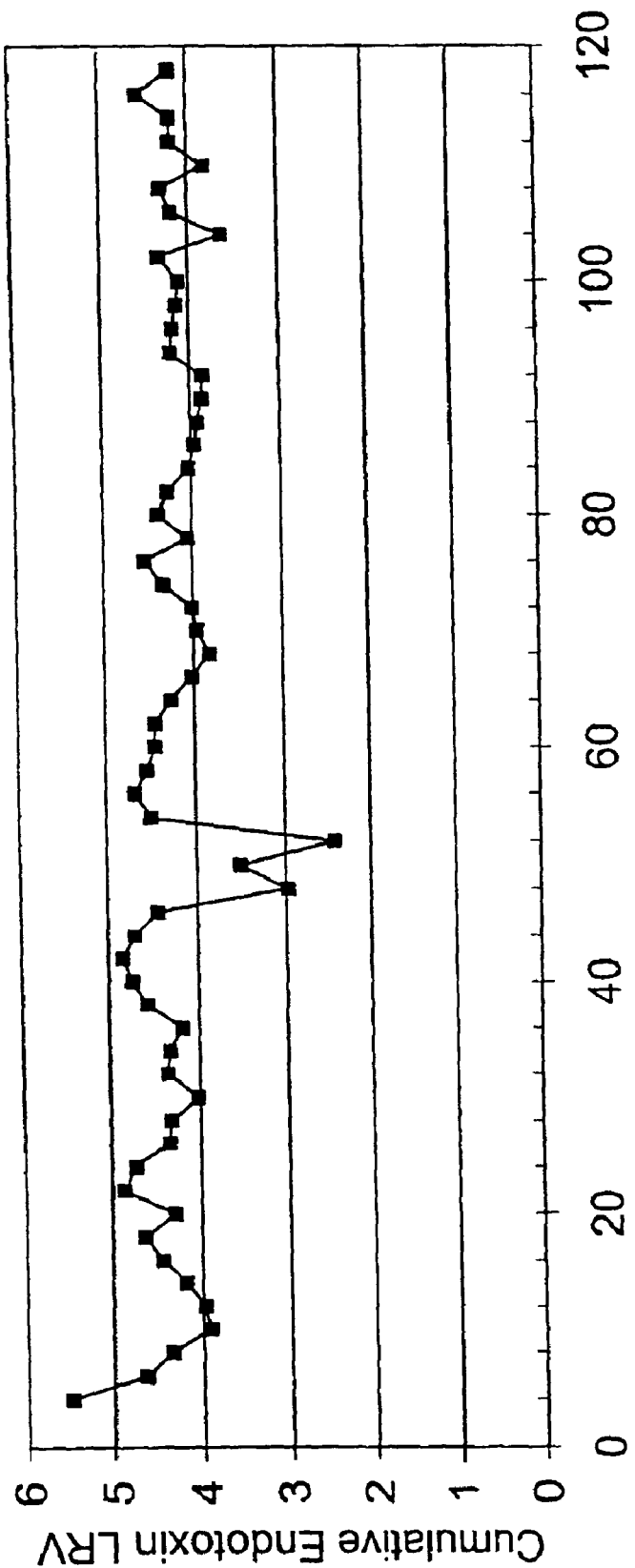
In FIGS. 1–6, the x-axis depicts the filtrate fraction collection time in minutes and the y-axis depicts the Log Reduction Value, which is defined as $\text{Log}_{10}$(endotoxin challenge concentration/endotoxin concentration in the fraction).

The present invention is predicated on the discovery that a hydrophilic membrane having fixed charges and a hydrophobic component has excellent retention of bacterial contaminants, for example, endotoxins.

The present invention provides, in one embodiment, a hydrophilic charged microporous membrane comprising a porous hydrophobic substrate and a coating comprising a charge-providing agent. The charge-providing agent contains a suitable positively or negatively charged group. An example of a positively charged group is quaternary ammonium. Preferably, the charge-providing agent is a polymer. When utilized in a coating, the charge-providing agent is believed to also coat the pore walls of the substrate. The coating preferably comprises a polyamine containing quaternary ammonium groups. It is further preferred that the polyamine is crosslinked, e.g., through the ring opening reaction of an epoxy group.

Examples of preferred positively charged polymers include polyethyleneimines, more preferably polyethyleneimines modified to contain quaternary ammonium groups. Illustratively, a modified polyethyleneimine can be prepared by reacting a polyethyleneimine with epichlorohydrin such that some or all of the tertiary amino groups on the polyethyleneimine are converted to quaternary ammonium groups. Such epichlorohydrin modified polyethyleneimines can be obtained commercially. For example, LUPASOL™ SC-86×is an epichlorohydrin modified polyethyleneimine available from BASF Corporation in Mount Olive, N.J.

Preferably, the positively charged polymer further includes a polydimethylamine, e.g., a quaternized poly (dimethylamine-co-epichlorohydrin). One example of a suitable quaternized poly(dimethylamine-co-epichlorohydrin) is available as Catalog No. 652, Scientific Polymer Products, Inc., Ontario, N.Y.

The polyamines used in the present invention are preferably water soluble or made water soluble by suitable chemical modifications, for example, by introducing hydrophilic groups such as hydroxyl.

As discussed above, the charge-providing agent can be positively or negatively charged. In a negatively charged embodiment, the charge-providing agent can be a negatively charged polymer. The negatively charged polymer can contain any suitable negative group, preferably a sulfonic acid group. For example, the negatively charged polymer comprises a polymerized acrylamidosulfonic acid monomer, preferably an acrylamidoalkyl sulfonic acid monomer. An example of such a monomer is 2-acrylamido-2-methyl-1-propanesulfonic acid ("AMPS").

It is further preferred that the negatively charged polymer is crosslinked. Although the crosslinking can be accomplished by any crosslinking agent, a preferred crosslinking agent is an acrylamido crosslinking agent. An example of an acrylamido crosslinking agent is N-(alkoxymethyl) acrylamide, preferably N-(isobutoxymethyl)acrylamide ("IBMA").

Optionally, the negatively charged polymer can include a polymerized hydroxyalkyl acrylate monomer, for example, a hydroxyethyl acrylate such as a hydroxyethyl alkylacrylate, e.g., 2-hydroxyethyl methacrylate. The term "alkyl" herein refers to lower alkyl groups, particularly, $C_1$–$C_{10}$ alkyl, and more particularly, $C_1$–$C_3$ alkyl groups.

The present invention thus provides a process for preparing an embodiment of the hydrophilic charged membrane comprising a porous hydrophobic substrate and a coating comprising a charge-providing agent comprising contacting a porous hydrophobic substrate with a composition comprising a charge-providing agent or a precursor thereof.

The hydrophobic substrate can be made of any suitable material; preferably, the substrate comprises a hydrophobic polymer. Examples of hydrophobic polymers include polysulfones, polyolefins, polystyrenes, polyaromatics, cellulosics, polyesters, polyamides such as aromatic polyamides and aliphatic polyamides having long alkyl segments, e.g., $C_8$–C16 segments, polyimides, polytetrafluoroethylene, polycarbonates, and PEEK. Aromatic polysulfones are preferred. Examples of aromatic polysulfones include polyethersulfone, bisphenol A polysulfone, and polyphenylsulfone. Polyethersulfone is particularly preferred. The porous hydrophobic substrate can have any suitable pore size, for example, a pore size of about 10 μm or less, e.g., in the range of from about 0.1 μm to about 10 μm, preferably from about 0.1 μm to about 5 μm, and more preferably from about 0.2 μm to about 1 μm.

The porous hydrophobic substrate can be prepared by methods known to those of ordinary skill in the art. For example, it can be prepared by a phase inversion process. Thus, a casting solution containing the hydrophobic polymer, a solvent, a pore former, and optionally a small quantity of a non-solvent is prepared by combining and mixing the ingredients, preferably at an elevated temperature. The resulting solution is filtered to remove any insolubles or impurities. The casting solution is cast or extruded in the form of a sheet or hollow fiber. The resulting sheet or fiber is allowed to set or gel as a phase inverted membrane. The set membrane is then leached to remove the solvent and other soluble ingredients.

An embodiment of the hydrophilic charge modified membrane can be prepared as follows. The porous hydrophobic substrate is contacted with a composition comprising a charge providing agent or a precursor thereof. The contacting is carried out such that the charge-providing agent or precursor(s) thereof preferably coat the pore walls of the hydrophobic substrate. Thus, for example, the charge-providing agent or its precursor(s) can be dissolved in a suitable solvent that is compatible with the hydrophobic substrate to provide a solution that is subsequently placed in contact with the substrate.

Preferred solvents include water, low boiling alcohols such as methanol, ethanol, and isopropanol, and combinations thereof. Thus, for example, a mixture of water and ethanol is preferred. The solvent or the mixture of solvents is present in an amount of from about 80% to about 99% by weight, and preferably in an amount of from about 88% to about 97% by weight, of the coating composition.

To prepare a positively charged membrane, the polyamine or the mixture of polyamine precursors is typically present in an amount of from about 0.5% to about 20% by weight, and preferably in an amount of from about 1% to about 90% by weight, of the coating composition. In addition, the casting solution may contain a pH adjusting agent, e.g., to provide a pH level of from about 9.5 to about 11.5, and preferably from about 10.5 to about 11.0. The pH can be adjusted by the use of a base, e.g., an alkali such as potassium hydroxide.

The porous hydrophobic substrate can be coated with the coating solution by methods known to those of ordinary skill in the art, for example, by dip coating, spray coating, meniscus coating, and the like. Dip coating, for example, can be carried out as follows. The substrate is immersed in the solution for a suitable period of time. For example, the immersion time can be from about 1 second to about 15 minutes, preferably from about 2 seconds to about 15 seconds, and more preferably from about 3 seconds to about 5 seconds.

Following the immersion, the excess coating solution on the substrate is allowed to drain or is removed, e.g., by means of a squeegee or air knife. The resulting coated substrate is heated to remove the solvent, and, in certain embodiments, to allow the precursors to cure into a charge-providing polymeric agent. Thus, for example, a water/ethanol solution of the precursors, e.g., epichlorohydrin modified polyethyleneimine and quaternized poly (dimethylamine-co-epichlorohydrin), and a base, for example, potassium hydroxide, is prepared.

A hydrophobic substrate, for example, a polyethersulfone membrane sheet, is immersed in the coating solution for about 3 seconds. The excess solution is drained off the membrane, and the membrane is then allowed to cure, e.g., in a convection oven, at a temperature of from about 90° C. to about 150° C., and preferably from about 130° C. to about 140° C., for a suitable period of time. Thus, for example, the membrane can be cured at 135° C. for a period of from about 15 minutes to about 30 minutes. The resulting membrane can be washed to leach out any extractable in the membrane. Illustratively, the membrane can be leached in boiling deionized water. The resulting membrane is then dried in air or in an oven to remove the water.

To prepare a hydrophilic membrane comprising a porous hydrophobic substrate and a coating comprising a negative charge-providing agent, a hydrophobic substrate is contacted with a composition comprising a negative charge-providing agent or precursor thereof. For example, a polymeric precursor of the negative charge-providing agent, such as a prepolymer prepared from AMPS and IBMA, can be prepared first. A solution of this precursor can be contacted with the porous hydrophobic substrate. The contacted substrate can be dried and cured as described above.

In another embodiment, the present invention provides a hydrophilic charged microporous membrane comprising a porous hydrophobic polymeric matrix and a charge-providing agent distributed within the porous hydrophobic polymeric matrix. Without intending to be bound to any one theory or mechanism, it is believed that the charge-providing agent is distributed as a precipitate, occlusion, blend, and/or network within the hydrophobic matrix. Preferably, the charge-providing agent is not applied as a coating on the pore walls of the matrix. Thus, for example, the hydrophilic charged membrane is composed of a porous hydrophobic polymer such as polyethersulfone having a charge-providing agent containing positively or negatively charged groups dispersed therein. Such membranes can be produced by, e.g., co-casting, as illustrated below.

The present invention provides a process for preparing a hydrophilic positively charged membrane comprising casting a membrane from a casting solution comprising a hydrophobic polymer capable of forming the hydrophobic porous matrix, a solvent for the hydrophobic polymer, a pore former, and a charge-providing agent or a precursor thereof.

Any suitable hydrophobic polymer, solvent, and/or pore former can be used to prepare the hydrophobic matrix. Examples of hydrophobic polymers include polysulfones, polyolefins, polystyrenes, polyaromatics, cellulosics, polyesters, polyamides such as aromatic polyamides and aliphatic polyamides having long alkyl segments, e.g., $C_8$–$C_{16}$ segments, polyimides, polytetrafluoroethylene, polycarbonates, and PEEK. Aromatic polysulfones are preferred. Polyethersulfone is particularly preferred. N-methylpyrrolidone and N,N-dimethylformamide are preferred solvents. Polyethyleneglycol and glycerol are preferred pore formers.

The casting solution can be prepared by combining and mixing the required ingredients. To prepare a positively charged membrane, the positive charge-providing agent preferably contains quaternary and/or tertiary ammonium groups. It is preferred that the charge-providing agent is a polymer. The precursor of the polymeric charge providing agent includes one or more polymerizable monomers, an initiator, and, optionally, a crosslinking agent. Suitable monomers include acrylic monomers, e.g., acryloyl monomer, and more preferably, an alkyl substituted acryloyl or alkacryloyl monomer. It is further preferred that the monomer is an alkacryloylaminoalkyl monomer. The term "alkyl" herein refers to lower alkyl groups, particularly, $C_1$–$C_{10}$ alkyl, and more particularly, $C_1$–$C_3$ alkyl groups.

A combination of charged monomers and uncharged monomers can be employed. The uncharged monomer, when polymerized, is believed to provide advantageous charge separation and/or improved compatibility between the charge-providing agent and the hydrophobic matrix.

An example of a preferred alkacryloylaminoalkyl monomer is methacryloylaminopropyl monomer. The positive charge-providing agent can be a polymer comprising methacyloylaminopropyl trimethylammonium groups. An example of a suitable precursor is selected from the group consisting of N-{3-(dimethylamino)propyl}-methacrylamide, {3-(methacryloylamino)propyl}-trimethylammonium chloride, and combinations thereof.

Preferably, the charge-providing polymer is crosslinked. Any suitable crosslinking agent known to those of ordinary skill in the art can be used. Preferably, a polyfunctional crosslinking agent such as a polyacrylate, e.g., di, tri-, or higher acrylate, can be used. Alkyleneglycol polyacrylates, particularly, alkyleneglycol diacrylates are preferred. The term "alkylene" herein denotes a $C_2$–$C_{10}$ alkylene moiety of, and preferably, a $C_2$–$C_4$ moiety. Alkyleneglycol dialkylacrylates are further preferred. The term "alkyl" herein refers to lower alkyl groups, particularly, $C_1$–$C_{10}$ alkyl, and more particularly, $C_1$–$C_3$ alkyl groups. Alkyleneglycol dimethacrylates are further preferred. A suitable example of an alkyleneglycol dimethacrylate is ethyleneglycol dimethacrylate. Additional examples of alkyleneglycol dimethacrylates include di, tri-, and higher ethyleneglycol dimethacrylates and polyethyleneglycol dimethacrylate. In addition to, or in place of, alkyleneglycol dimethacrylates, di-, tri-, and higher alkyleneglycol dialkyl acrylates such as diethyl, dipropyl, and higher dialkylacrylates can be used.

Any suitable polymerization initiator can be used, preferably a free radical polymerization initiator. Ammonium persulfate is an example of a suitable free radical initiator.

The ingredients that make up the casting solution can be combined in any suitable proportion. Illustratively, the hydrophobic polymer can be present in an amount of from about 6% to about 22% by weight, and preferably from about 9% to about 15% by weight of the casting solution. The solvent can be present in an amount of from about 15% to about 30% by weight, and preferably from about 18% to about 30% by weight, of the casting solution. The pore former can be present in an amount of from about 50% to about 80% by weight, and preferably from about 60% to about 70% by weight, of the casting solution.

Typically, the charged monomer is present in an amount of from about 0.01% to about 15% by weight, and preferably from about 1.5% to about 2.5% by weight, of the casting solution prior to polymerization.

Illustratively, the crosslinking agent can be present in an amount of from about 0.001% to about 2% by weight, and preferably from about 0.03% to about 1% by weight, of the casting solution prior to polymerization. By way of example, the initiator can be present in an amount of from about 0.01% to about 1% by weight, and preferably from about 0.05% to about 0.3% by weight, of the casting solution prior to polymerization.

The ingredients can be combined and mixed, preferably at an elevated temperature, in a suitable mixer. Thus, for example, the hydrophobic polymer can be added to the pore former in a suitable container equipped with a blender. The free radical initiator is dissolved in the solvent for the hydrophobic polymer and added to the container. The crosslinking agent and the precursor are then added. For example, the mixture is blended at a temperature of from about 90° F. (32° C.) to about 150° F. (65° C.) preferably from about 100° F. (49° C.) to about 140° F. (60° C.). The mixing can be carried out for a suitable length of time. Thus, for example, the mixture can be agitated at about 115° F. (46° C.) for about 8 hours. During the mixing, the precursor (s) undergo(es) polymerization. However, it is preferable not to advance the polymerization past the point where a precipitate or gel would form since precipitates and gels could adversely affect the casting operation or the quality of the resulting membrane. The resulting casting solution can be filtered to remove any insolubles, precipitates, gels, or impurities. The casting solution can be advantageously degassed to remove bubbles.

The casting solution can be shaped into any suitable form, e.g., a sheet, a tube, or a hollow fiber. Thus, for example, the casting solution can be shaped into a sheet by extruding through a slit or by spreading on a glass plate using a doctor blade. The casting solution can also be spread as a thin film on a porous fabric or paper.

The casting solution shaped as above provides a pre-membrane. The pre-membrane is then allowed to undergo phase inversion. Phase inversion can be caused, e.g., by exposing the pre-membrane to a non-solvent liquid or vapor. Thus, for example, the pre-membrane can be exposed to water vapor in a controlled humidity chamber.

The resulting phase inverted membrane can be washed to remove the solvent, the pore former, and other washable ingredients. The phase-inverted membrane can be washed or leached in deionized water. The washed membrane is then dried to remove the water.

To prepare a hydrophilic membrane comprising a hydrophobic polymer matrix and a negative charge-providing agent distributed in the matrix, a negative charge-providing agent or a precursor thereof can be used. For example, a negatively charged monomer or a polymer can be included in the preparation of the membrane casting solution.

Thus, e.g., a mixture of AMPS and IBMA can be polymerized in a suitable solvent to obtain a copolymer solution as discussed in U.S. Pat. No. 5,021,160, the disclosure of which is incorporated herein in its entirety by reference. This copolymer solution can be combined with the hydrophobic polymer, the casting solvent(s), the pore formers, the initiator, the crosslinking agent, and other ingredients as discussed above. The resulting mixture can be heated to obtain a casting solution. The negatively charged membrane can be prepared by casting the solution and causing phase inversion. The copolymer solution preferably contains a copolymer in an amount of from about 5% to about 20% by weight and more preferably in an amount of from about 10% to about 15% by weight of the solution. The copolymer can be used in an amount of from about 0.1% to about 1.5% by weight and more preferably in an amount of from about 0.3% to about 0.5% by weight of the casting solution.

The porous hydrophobic matrix can have any suitable pore size, for example, a pore size of about 10 $\mu$m or less, e.g., in the range of from about 0.1 $\mu$m to about 10 $\mu$m, preferably from about 0.1 $\mu$m to about 5 $\mu$m, and more preferably from about 0.2 $\mu$M to about 1 $\mu$m.

The present invention further provides a filter comprising the hydrophilic charged membranes of the present invention. The filter can be in any suitable form. For example, the filter can include a filter element made of the hydrophilic charged membrane sheet. In a preferred embodiment, the filter is disposed in a housing to provide a filter device.

The membranes of the present invention have excellent water permeability, endotoxin binding capacity, and, preferably, charge density. Thus, for example, the hydrophilic charged microporous membrane comprising a hydrophobic porous substrate and a coating comprising a positive charge-providing agent has a water flow rate of from about 15 to about 35 mL/minute/cm$^2$, and preferably from about 19 to about 24 mL/minute/cm$^2$, at 10 psi (0.68 bar). The above membrane has a nominal pore size of 0.2 $\mu$m, typically, an open water bubble point of from about 52 to about 69 psi (about 3.5 to about 4.7 bar), and preferably from about 55 to about 59 psi (about 3.7 to about 4.0 bar).

The above positively charged membrane is wet by a 25% NaCl aqueous solution in a period of time less than 5 seconds, preferably from about 3 seconds to about 4 seconds. The above membrane is wet by a 20% NaCl aqueous solution in a period of time less than 3 seconds, preferably from about 1 second to about 2 seconds. Deionized or pure water as well as aqueous NaCl solutions of up to 15% by weight wet the membrane instantly, i.e., in less than 1 second.

The above membrane preferably has a high charge density. The charge density can be measured by any suitable method, e.g., by an electrolytic method such as measuring the potential drop across the membrane when it is placed between two electrolyte solutions of differing ionic strength; or, by a dye-binding method.

Illustratively, for positively charged membranes, the binding capacity can be measured by using a negatively charged dye such as Metanil Yellow. For negatively charged membranes, the binding capacity can be measured using a positively charged dye such as Methylene Blue.

Thus, for example, the above positively charged membrane has a Metanil Yellow Dye binding capacity of up to 500 mL or more, e.g., from about 200 mL to about 400 mL, and preferably from about 300 mL to about 350 mL. The dye binding capacity can be measured by, for example, filtering under a $\Delta$P of 10 psi (0.68 bar), a 10 ppm by weight solution, pH 6.6, of Metanil Yellow Dye in a membrane disc of 3.7 square centimeters, and monitoring the volume of the filtrate until a trace of the dye begins to appear in the filtrate. In a preferred embodiment, the above positively charged membrane has an endotoxin binding capacity of at least about 100,000 EU/cm$^2$, e.g., from about 120,000 EU/cm$^2$ to about 200,000 EU/cm$^2$ or greater, and preferably greater than about 130,000 EU/cm$^2$, in water as well as in 0.9% saline.

The hydrophilic charged microporous membrane comprising a hydrophobic porous substrate and a coating comprising a negative charge-providing agent has a water flow rate of from about 5 to about 35 mL/minute/cm$^2$, and preferably from about 18 to about 28 mL/minute/cm$^2$, at 10 psi (0.68 bar). The above membrane has a nominal pore size of 0.2 $\mu$m, and typically, an open water bubble point of from about 50 to about 65 psi (about 3.4 to about 4.4 bar), and preferably from about 52 to about 59 psi (about 3.5 to about 4.0 bar). In a preferred embodiment, the above membrane has an endotoxin binding capacity of at least about 100,000 EU/cm$^2$, e.g., from about 100,000 EU/cm$^2$ to about 300,000 EU/cm$^2$ or greater, and preferably greater than about 223,000 EU/cm$^2$, in 0.9% saline. The membrane had a Methylene Blue Dye binding capacity of 320 mL.

The hydrophilic charged membrane comprising a positive charge-providing agent distributed within a hydrophobic matrix typically has a water flow rate of at least about 10 mL/minute/cm², e.g., from about 15 mL/minute/cm² to about 50 mL/minute/cm², and preferably from about 18 mL/minute/cm² to about 35 mL/minute/cm², at 10 psi (0.68 bar). The above membrane has an open water bubble point of from about 45 psi to about 70 psi (about 3.1 to about 4.8 bar), and preferably from about 50 psi to about 60 psi (about 3.5 to about 4.1 bar).

A 20% NaCl solution wets the above membrane in a period of from about 5 seconds to about 1 second, and preferably, instantly. The above membrane preferably has a high charge density. Thus, in some embodiments, the membrane has a Metanil Yellow Dye binding capacity of 100 mL to about 600 mL, and preferably from about 200 mL to about 300 mL. Typically, the membrane has an endotoxin binding capacity of at least about 100,000 EU/cm², e.g., from about 130,000 EU/cm² to about 600,000 EU/cm² or greater, and preferably greater than 500,000 EU/cm² in 0.9% saline. The membrane has an endotoxin binding capacity of at least about 100,000 EU/cm², e.g. from about 130,000 EU/cm² to about 900,000 EU/cm² or greater, and preferably greater than 800,000 EU/cm² in water.

The hydrophilic charged membrane comprising a negative charge-providing agent distributed within a hydrophobic matrix typically has a water flow rate of at least about 10 mL/minute/cm², e.g., from about 15 mL/minute/cm² to about 50 mL/minute/cm², and preferably from about 18 mL/minute/cm² to about 35 mL/minute/cm², at 10 psi (0.68 bar). The above membrane has an open water bubble point of from about 45 psi to about 70 psi (about 3.1 to about 4.8 bar), and preferably from about 50 psi to about 60 psi (about 3.5 to about 4.1 bar).

A 15% NaCl solution wets the above membrane in a period of from about 5 seconds to about 1 second, and preferably, instantly. The above membrane preferably has a high charge density. Illustratively, in some embodiments, the membrane has a Methylene Blue Dye binding capacity of 5 mL to about 50 mL, and preferably from about 10 mL to about 20 mL. The membrane has an endotoxin binding capacity of at least about 100,000 EU/cm², e.g., from about 100,000 EU/cm² to about 300,000 EU/cm² or greater, and preferably greater than 200,000 EU/cm² in 0.90/o saline.

An advantage of a preferred embodiment of the present invention is that the components of the novel membranes are carefully chosen so that the membranes are free or substantially free of grafts or covalent links between the charge modifying agent and the hydrophobic substrate or matrix. The preparation of the hydrophilic charged membranes of the present invention involve chemistries and procedures that are relatively simple and/or easy to practice.

The properties of the membranes of the present invention make the membranes attractive for use in the removal of bacterial contaminants, particularly, lipopolysaccharides and/or lipoteichoic acids, from biological and pharmaceutical products. For example, bacterial contaminants can be removed from biological fluids, pharmaceutical products, buffers, salt solutions, dialysis solutions, and cell growth media, as well as from other biological preparations. A biological fluid includes any treated or untreated fluid associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate, platelet-rich plasma, platelet-poor plasma, platelet-free plasma, plasma, fresh frozen plasma, components obtained from plasma, packed red cells, transition zone material or buffy coat; analogous blood products derived from blood or a blood component or derived from bone marrow, red cells separated from plasma and resuspended in physiological fluid; and platelets separated from plasma and resuspended in physiological fluid. The biological fluid may have been treated to remove some of the leukocytes before being processed according to the invention. Sometimes, reference is made to a "unit" of a biological fluid. A "unit" is the quantity of biological fluid from a donor or derived from one unit of whole blood. It may also refer to the quantity drawn during a single donation. Typically, the volume of a unit varies, the amount differing from patient to patient and from donation to donation. Multiple units of some blood components, particularly platelets and buffy coat, may be pooled or combined, typically by combining four or more units.

As used herein, biological fluid refers to the components described above as well as to lymph fluids, and cerebrospinal fluid. Pharmaceutical products include compositions comprising proteins (e.g., antibodies, enzymes, vaccines), amino acids, peptides, nucleic acids, plasmids, cosmids, phages, polysaccharides, lipids, bioreactor, fermentor and/or cell culture harvests.

The membranes of the present invention are suitable for reducing endotoxin contamination from samples-containing plasmids and endotoxins. Embodiments of the membrane can reduce endotoxins present in nucleic acid (e.g., DNA) samples from over 1000 EU/mL of a fluid to less than 10 EU/mL (>2 logs). The endotoxin concentration can be reduced from over 52,000 EU/mg of DNA to less than 500 EU/mg DNA. The DNA can be chromosomal or extrachromosomal.

Thus, the present invention provides a process for treating a fluid containing bacterial contaminants to deplete the contaminants therefrom, the process comprising placing the fluid in contact with the hydrophilic charged membrane and recovering a bacterial contaminant-depleted fluid.

The contaminated fluid can be contacted with the membrane, for example, by passing the liquid through a filter containing the membrane of the present invention. Illustratively, the fluid is contacted with the membrane by passing the fluid under pressure over or through the membrane surface. Thus, the fluid can be passed through a filter, and the contaminant depleted filtrate (e.g., permeate) can be collected, further processed and/or administered or returned to a patient.

The present invention further provides a device, e.g., a filter device, chromatography device, macromolecular transfer device, flow distributor arrangement, and/or a membrane module comprising one or more inventive membranes of the present invention. In some embodiments of the invention, a set and/or system is provided, comprising a filter device including the inventive membrane, and at least one of a container, conduit, and vent. One embodiment of a system includes an additional filter device such as a leukocyte filter device.

The device can be in any suitable form. Typical filter devices comprise a housing including at least one inlet and at least one outlet defining a fluid flow path between the inlet and the outlet, and a membrane of the present invention disposed across the fluid flow path or tangentially to the fluid flow path. In some embodiments, e.g., wherein the filter device is suitable for processing fluid to be returned and/or administered to a patient, the device can include additional components such as, for example, at least one vent, e.g., at least one gas outlet and/or at least one gas inlet. Typically, the vent includes a porous medium that allows gas to pass therethrough while preventing the passage of bacterial therethrough.

Illustratively, the device can include a filter element comprising the inventive membrane in a substantially planar or pleated form. In an embodiment, the element can have a hollow generally cylindrical form. If desired, the device can include the filter element in combination with upstream and/or downstream support or drainage layers. The device can include a plurality of membranes, e.g., to provide a multilayered filter element, or stacked to provide a membrane module, such as a membrane module for use in membrane chromatography. For embodiments of the membrane which are in the form of a tube or fiber, bundles of tubes or fibers can be converted into modules by potting their ends by the use of an adhesive. Filter cartridges can be constructed by including a housing and endcaps to provide fluid seal as well as at least one inlet and at least one outlet.

The devices can be constructed to operate in crossflow or tangential flow mode as well as dead-end mode. Accordingly, the fluid to be treated can be passed, for example, tangentially to the membrane surface, or passed perpendicular to the membrane surface.

The following examples further illustrate the present invention, but of course, should not be construed as in any way limiting its scope.

EXAMPLE 1

This Example illustrates a method of preparing a membrane of the present invention by the phase inversion method and its properties.

| Ingredients | Wt. % |
|---|---|
| Polyethyleneglycol | 62.3 |
| Polyethersulfone | 13.0 |
| Deionized water | 1.5 |
| Glycerol | 1.0 |
| N,N-Dimethylformamide | 10.0 |
| N-methylpyrrolidone | 7.6 |
| Ammonium persulfate | 0.1 |
| Ethyleneglycol dimethacrylate | 1.5 |
| N-{3-(dimethylamino)propyl} methacrylamide | 1.5 |
| 3-{(Methacryloylamino)- propyl}trimethylammonium chloride | 1.5 |

The above ingredients were combined and mixed at 130° F. for 18 hours. The resulting solution was degassed and cast onto a supporting surface, and phase inversion was carried out by exposure to water vapor. The resulting membrane was washed with deionized water and dried. The membrane had an open water bubble point of 55 psi; a water flow rate of 25.5 mL/minute/cm$^2$ at 10 psi (0.68 bar); a thickness of about 6.0)6.1 mils (150–153 $\mu$m); and a Metanil Yellow Dye binding capacity of 386 mL, 10 ppm solution at pH 6.6, at a $\Delta$P of 10 psi (0.68 bar). A 15% NaCl solution wet the membrane instantly. The membrane had a nominal pore size of 0.2 $\mu$m

EXAMPLE 2

This Example illustrates the ability of the membrane described in Example 1 to retain endotoxin. The membrane was tested as follows. A 25 mm diameter membrane disk having an effective filtration area (EFA) of 3.7 cm$^2$ was challenged with a sterile, nonpyrogenic 0.9% Sodium Chloride for Injection USP (McGraw) spiked with a target of 10,000 EU/mL of purified E. coli 055:B5 endotoxin at a flow rate of 1 ml/min. Effluent fractions were collected and the endotoxin content of each fraction was determined using a kinetic, chromogenic Limulus Ameobocyte Lysate (LAL) assay (Charles River Labs Endochrome K kit). A standard curve was prepared by using sterile, nonpyrogenic 0.9% Sodium Chloride for Injection USP (saline) as the diluent The log reduction value (LRV) of each filtrate fraction was determined. The actual challenge endotoxin concentration was 15,543 EU/mL. The fluid flow rate was 1 ml/min. The LRV results obtained are shown graphically in FIG. 1. The membrane had an endotoxin binding capacity of greater than 504,097 EU/cm$^2$ in saline.

The endotoxin retention capacity (at LRV>2) of the membrane was calculated using the following formula: Capacity (LRV>2)=T×C/F×EFA, wherein T=total time LRV was greater than 2; C=endotoxin challenge concentration; and F=flow rate of endotoxin containing fluid.

Figure 2:
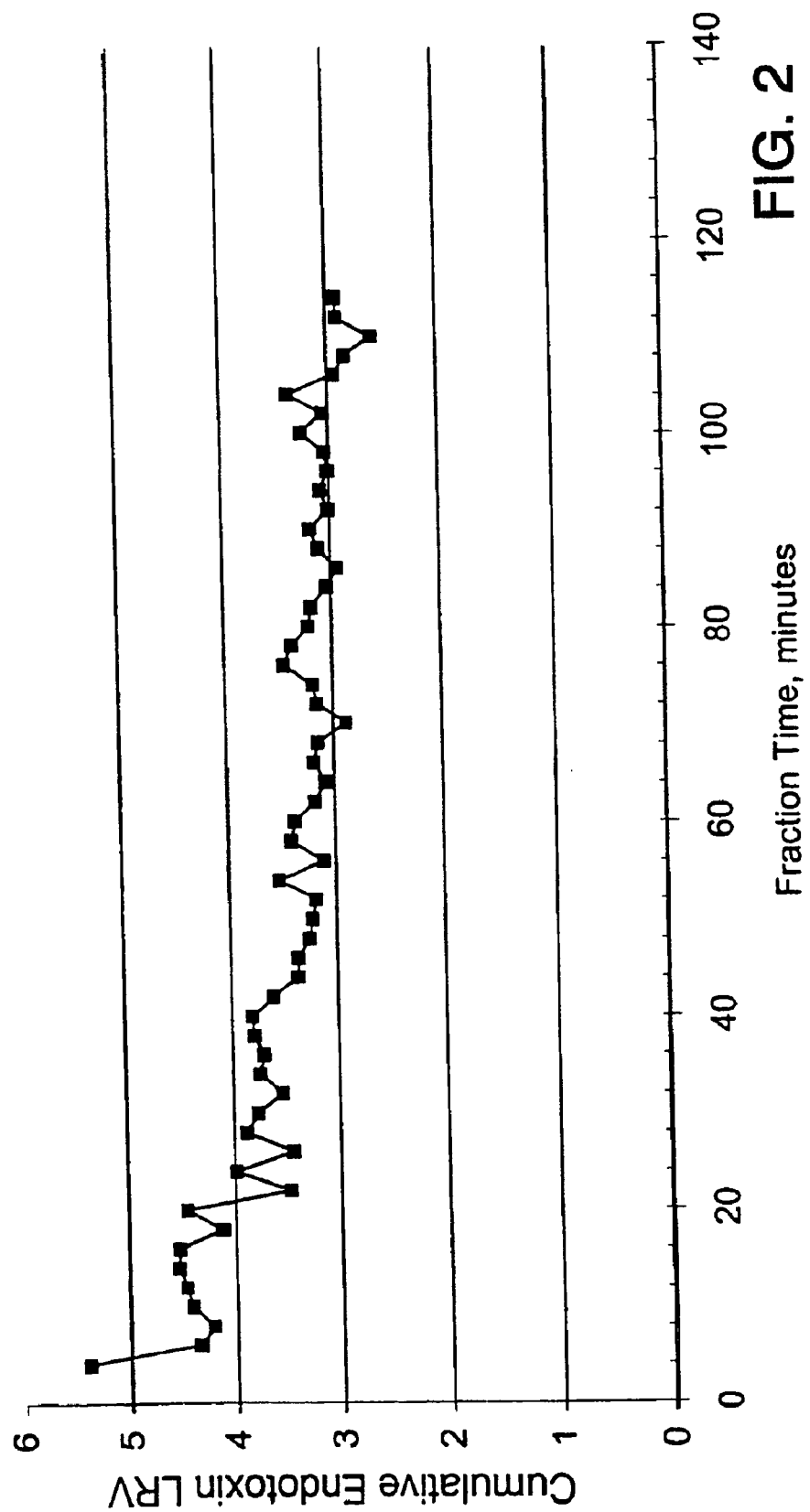

The membrane prepared in Example 1 was tested for endotoxin removal from water. The target endotoxin challenge concentration was 10,000 EU/mL. The actual challenge endotoxin concentration was 28,540 EU/mL. The fluid flow rate was 1 ml/min. The LRV results obtained are depicted in FIG. 2. The standard curve was prepared in deionized water. The membrane had an endotoxin binding capacity of greater than 863,913 EU/cm$^2$ in water.

The embodiments of membranes made in accordance with the present invention removed endotoxin with great effectiveness from saline and water.

EXAMPLE 3

This Example illustrates the preparation of a membrane comprising a hydrophobic porous substrate and coating comprising a charge-providing agent.

A hydrophobic porous polyethersulfone substrate was prepared from a casting solution containing polyethylene glycol 400 69.4%, polyethersulfone 13.0%, Reverse Osmosis treated water 1.5%, glycerol 3.5%, N,N-dimethylformamide 10.0%, and N-methylpyrrolidone 7.6%, all percentages by weight of the casting solution. The membrane had a nominal pore size of 0.2 pan.

A coating solution was prepared from the following ingredients.

| Ingredients | Wt. % |
|---|---|
| Water | 94.5 |
| Potassium hydroxide | 1.0 |
| Epichlorohydrin modified polyethyleneimine | 2.0 |
| Quaternized poly(dimethylamine-co-epichlorohydrin) | 2.5 |

The coating solution was prepared by combining and mixing the above ingredients for about 1 hour. The pH of the solution was adjusted to approximately 10.6 using a 20% potassium hydroxide solution immediately before use. The hydrophobic polyethersulfone was prewet in ethanol, rinsed in water, and then dipped in the coating solution. The coated membrane was cured at a temperature of about 135° C. for 30 minutes. The cured membrane was extracted in boiling deionized water and dried in air.

A membrane prepared as above had an open water bubble point of 54 psi; a water flow rate of 18.3 mL/minute/cm$^2$ at 10 psi (0.68 bar); a thickness of about 5.3 mils (133 µm); and a Metanil Yellow Dye binding capacity of 346 mL. The membrane was wet by 15%, 10%, and 5% NaCl aqueous solutions as well as deionized water instantly. The wetting time for a 20% NaCl solution was 1–2 seconds, and the wetting time for a 25% NaCl solution was 34 seconds.

EXAMPLE 4

This Example illustrates the ability of a membrane of the present invention described in Example 3 to retain endotoxin. The membrane was tested for endotoxin removal from water as well as from 0.90/o saline.

Figure 3:
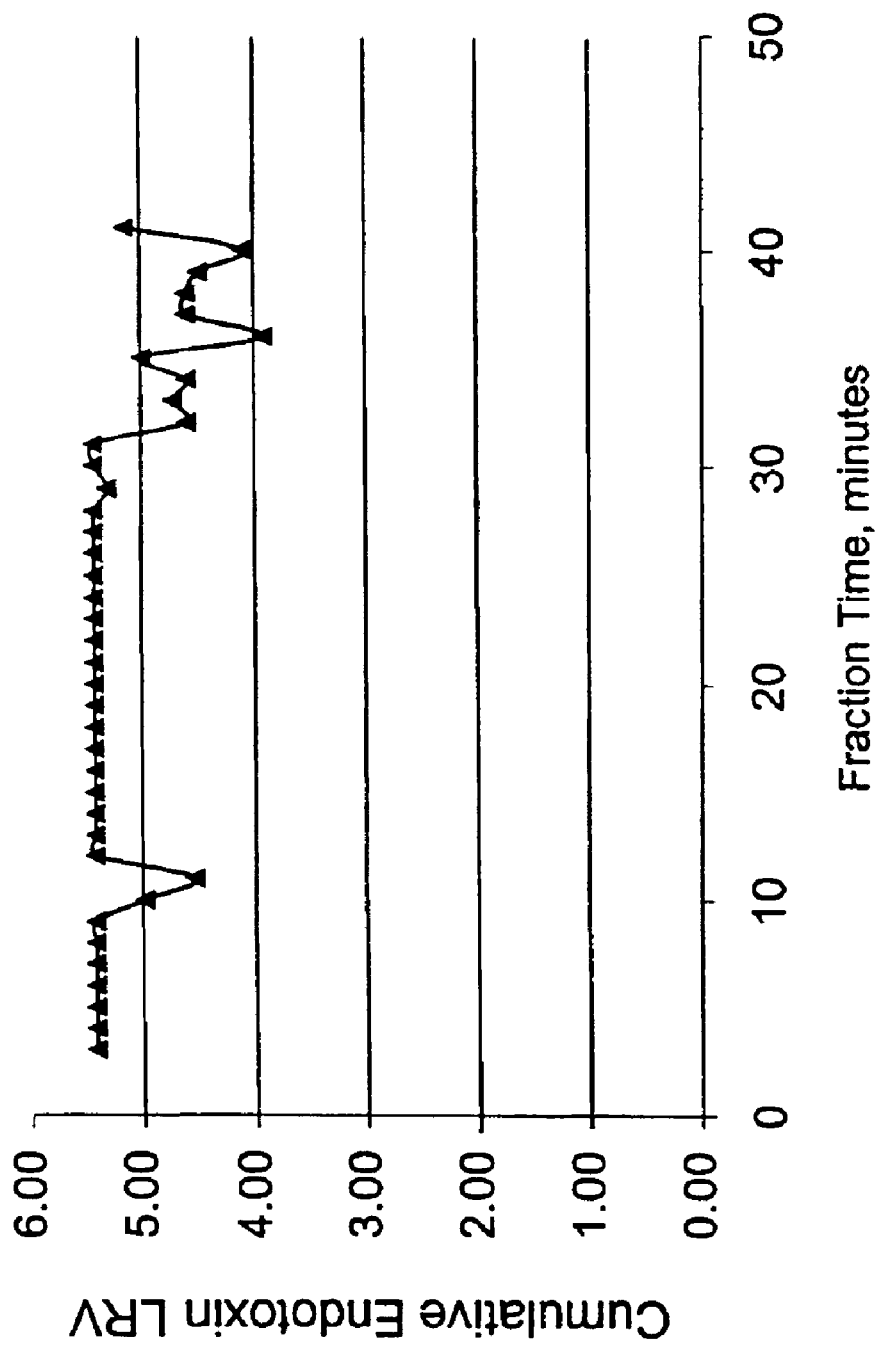

The LRV results obtained for the saline solution are depicted in FIG. 3. The target endotoxin challenge concentration was 10,000 EU/mL. The endotoxin concentration in the feed saline solution was measured at 12,780 EU/mL. The fluid flow rate was 1 ml/min. The membrane removed the endotoxin with great effectiveness. The detection limit of the assay was 0.05 EU/mL or an LRV of 5.4. The membrane had an endotoxin removal capacity of greater than 134,708 EU/cm$^2$ in saline.

Figure 4:
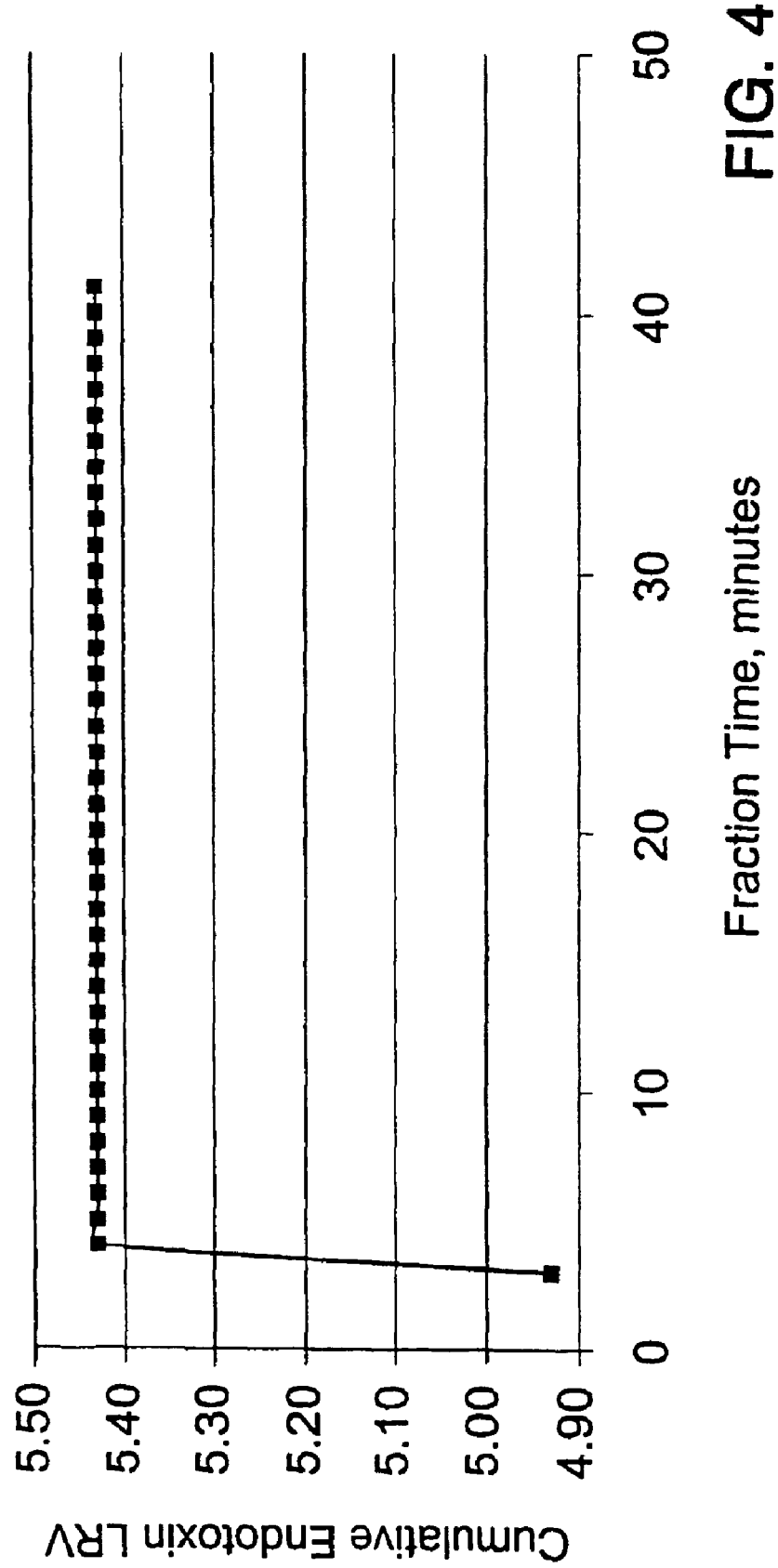

The LRV results obtained for water are depicted in FIG. 4. The water flow rate was 1 ml/min. The target endotoxin challenge concentration was 10,000 EU/mL. The actual endotoxin challenge concentration was 13,480 EU/mL. The membrane was effective in removing endotoxin and had an endotoxin binding capacity of greater than 142,086 EU/cm$^2$ in water.

EXAMPLE 5

This Example illustrates another embodiment of a membrane suitable for treating fluids containing a bacterial contaminant. The ingredients and their quantities are set forth below.

| Ingredients | Wt. % |
|---|---|
| Polyethyleneglycol | 63.3 |
| Polyethersulfone | 13.0 |
| Glycerol | 1.0 |
| N,N-Dimethylformamide | 10.0 |
| N-methylpyrrolidone | 7.6 |
| Ammonium persulfate | 0.1 |
| Ethyleneglycol dimethacrylate | 1.0 |
| IBMA-AMPS copolymer solution (12% by weight) | 4.0 |

The IBMA-AMPS copolymer solution was prepared from AMPS and IBMA as described in Example 1 of U.S. Pat. No. 5,021,160.

The ingredients set forth in the table above were combined and mixed at 130° F. (54.4° C.) for 18 hours. The resulting solution was degassed and cast onto a supporting surface, and phase inversion was carried out by exposure to water vapor. The resulting membrane was washed with deionized water and dried. The membrane had an open water bubble point of 53.9 psi; a water flow rate of 18.8 mL/minute/cm$^2$ at 10 psi (0.68 bar); a thickness of about 5.5–5.9 mils (137–148 µm); and a Methylene Blue Dye binding capacity of 16 mL, 10 ppm solution at pH 6.6, at a ΔP of 10 psi (0.68 bar). A 15% NaCl solution wet the membrane instantly. The membrane had 8 nominal pore size of 0.2 µm.

Figure 5:
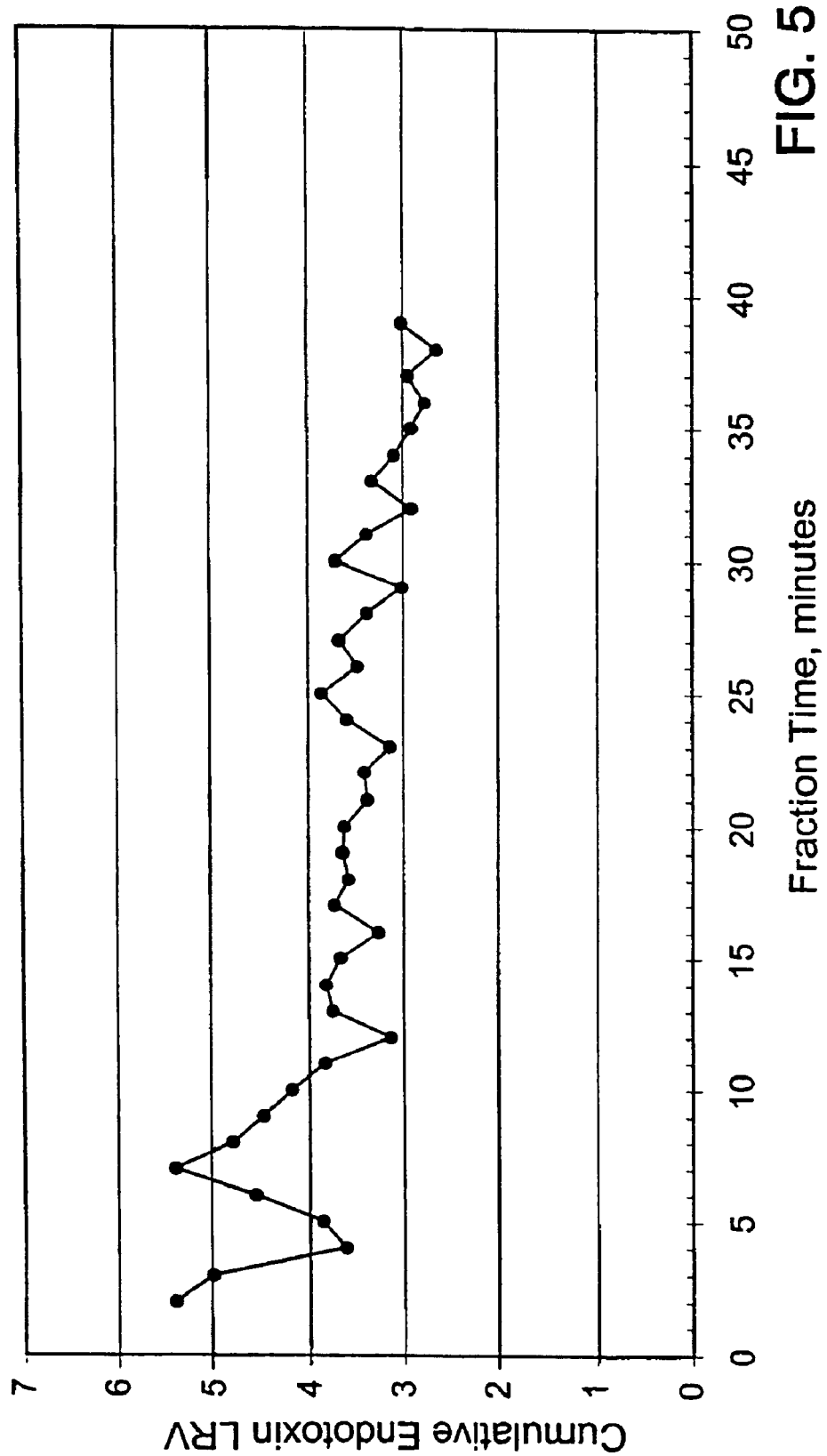

The membrane was tested for endotoxin removal from 0.9% saline as described in Example 2. The target endotoxin challenge concentration was 10,000 EU/mL. The actual endotoxin challenge level was 24,560 EU/mL. The fluid flow rate was 1 ml/min. The detection limit was 0.05 EU/mL or an LRV of 5.7. The results obtained are depicted in FIG. 5. The membrane had an endotoxin binding capacity of greater than 265,513 EU/cm$^2$ in saline.

EXAMPLE 6

Figure 6:
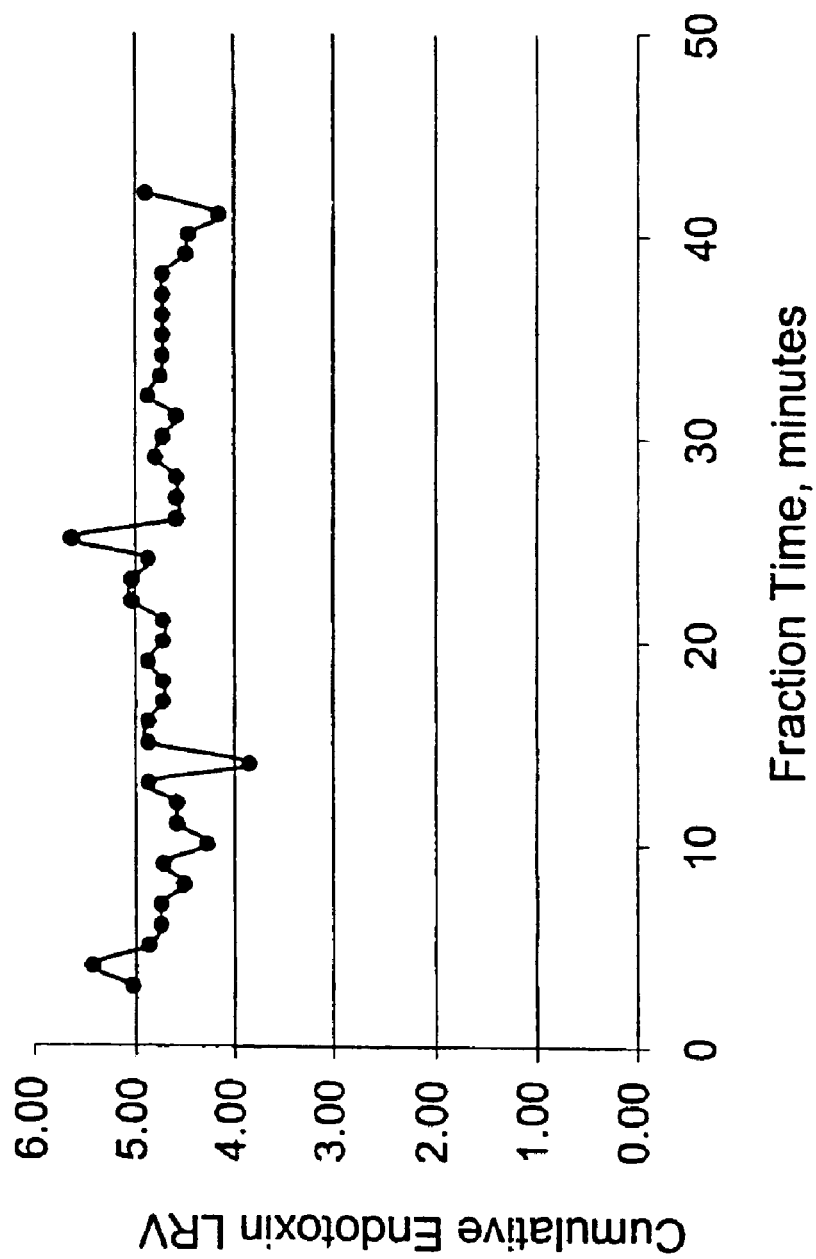

This Example illustrates another embodiment of a membrane suitable for treating fluids containing a bacterial contaminant A hydrophilic negatively charged membrane was prepared by coating a hydrophobic polyethersulfone porous substrate with a negative charge-providing coating comprising a polymer having sulfonic acid groups. The coating solution and the membrane were prepared as described in Examples 1–2 of U.S. Pat. No. 5,021,160. The membrane was tested for endotoxin removal from a 0.9% saline solution. The LRV results obtained are depicted in FIG. 6. The target endotoxin challenge concentration was 10,000 EU/mL. The actual endotoxin challenge concentration was 20,631 EU/mL. The fluid flow rate was 1 ml/min. The membrane had an endotoxin binding capacity of greater than 223,000 EU/cm$^2$ in saline.

EXAMPLE 7

This Example illustrates the ability of a membrane of the present invention to reduce endotoxin concentration in an endotoxin contaminated plasmid sample.

A sample solution containing the plasmid pGEM, at a concentration of 23 µg/mL and endotoxin at a concentration of $1.2 \times 10^3$ EU/mL in a 0.75M NaCl-50 mM Tris buffer at pH 8 was contacted with a 25 mm membrane disc (EFA=3.7 cm$^2$) prepared as described in Example 3. The flow rate of the sample solution was kept at 1 ml/min (linear flow rate 0.27 cm/min). One mL fractions of the eluate were collected, and the endotoxin concentrations were determined by the standard LAL ay after 1:10 dilution of the eluate fractions with pyrogen free water from ENDOSAFE™. The detection limit of the LAL assay was 0.5 EU/mL.

Figure 7:
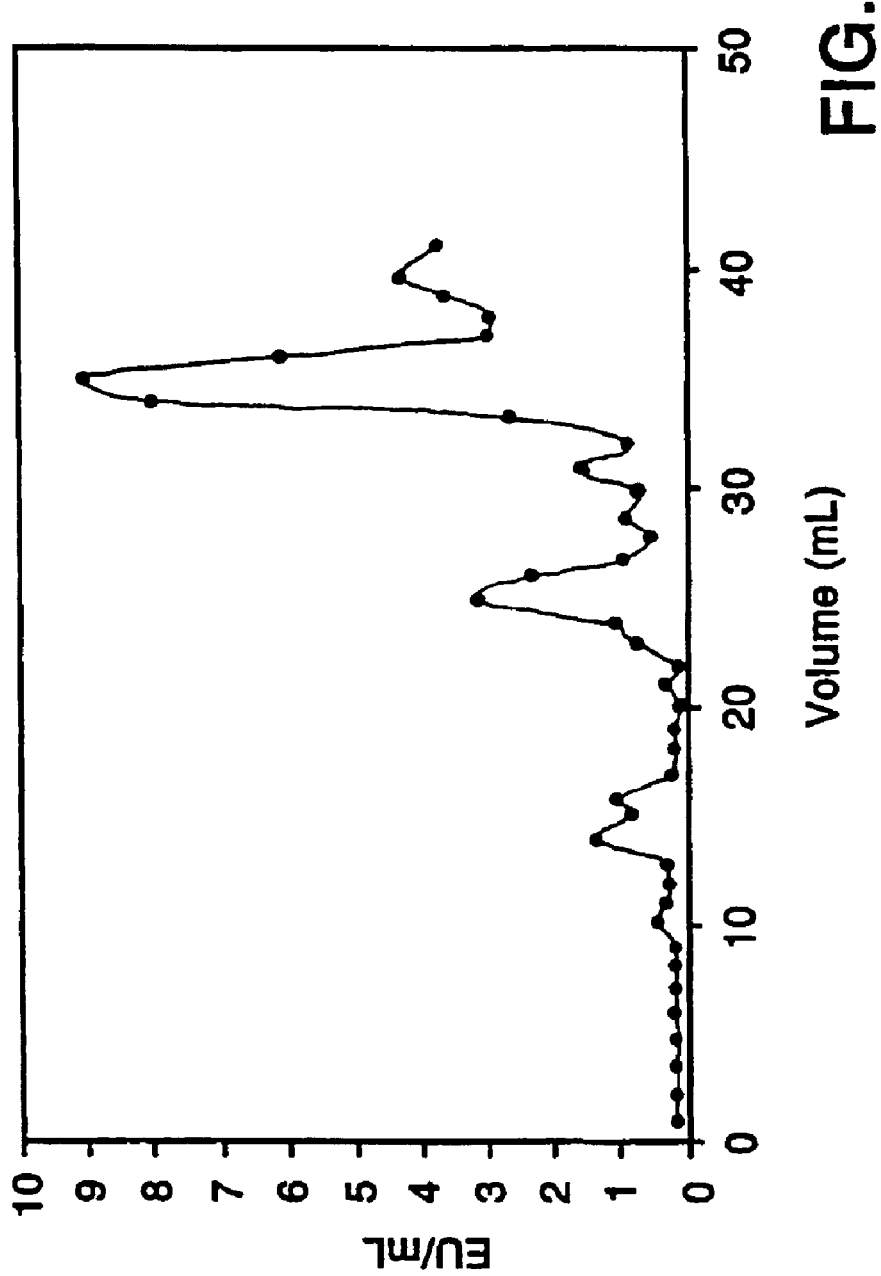
FIG. 7 depicts a breakthrough curve of endotoxin obtained during elution of an embodiment of a membrane that has been treated with a sample containing plasmid and endotoxin. The y-axis depicts the concentration of endotoxin in the eluate, and the x-axis depicts the number of the various eluate volume fractions.

The results obtained are set forth in FIG. 7. Endotoxin was undetectable in the first 10 fractions. The concentration of endotoxin was less than 2 EU/mL in fraction Nos. 11–20, less than 4 EU/mL in fiction Nos. 21–30, and less than 10 EU/mL in fractions Nos. 3141. The foregoing shows that the membrane reduced endotoxin levels in the sample.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A hydrophilic charged microporous membrane comprising a porous hydrophobic polyethersulfone matrix and a negatively charged charge-providing agent distributed within said porous hydrophobic polyethersulfone matrix, the charge-providing agent comprising a negatively charged polymer comprising a polymerized acrylamido sulfonic acid monomer and a polyacrylate.

2. The hydrophilic charged microporous membrane of claim 1, wherein said polyacrylate comprises ethyleneglycol dimethacrylate.

3. The hydrophilic charged microporous membrane of claim 1, wherein said porous hydrophobic matrix substantially free of a wetting agent.

4. A filter device comprising the membrane of claim 1 disposed in a housing.

5. A process for treating a fluid containing bacterial contaminants, said process comprising placing said fluid in contact with the hydrophilic charged microporous membrane of claim 1, and recovering a bacterial contaminant depleted fluid.

6. The process of claim 5, wherein said fluid is a pharmaceutical product.

7. A process for treating water containing bacterial contaminants comprising lipotechoic acid, said process comprising placing said water in contact with the hydrophilic charged microporous membrane of claim 1, and recovering bacterial contaminant depleted water.

8. The process of claim 7, wherein said bacterial contaminant includes endotoxin and wherein endotoxin depleted water is recovered.

9. A process for treating a saline solution containing bacterial contaminants, said process comprising placing said saline solution in contact with the hydrophilic charged microporous membrane of claim 1 and recovering a bacterial contaminant depleted saline solution.

10. The process of claim 9, wherein said saline solution has a surface tension of from about 72 to about 78 dynes/cm.

11. The process of claim 9, wherein said bacterial contaminant comprises an endotoxin.

12. The membrane of claim 1, wherein said membrane is wettable by a saline solution.

13. The hydrophilic charged microporous membrane of claim 1, which has an endotoxin binding capacity of at least about 100,000 EU/cm$^2$.

14. A process for preparing a hydrophilic charged microporous membrane comprising a porous hydrophobic matrix and a charge-providing agent distributed within said hydrophobic matrix, the process comprising forming a casting solution comprising a polymer capable of forming said porous hydrophobic matrix, a solvent for said polymer, a pore former, and a precursor of a charge-providing agent, wherein said precursor comprises a free radical polymerizable monomer, a crosslinking agent comprising a polyacrylate, and a free radical initiator.

15. The process of claim 14 further including causing phase-inversion to obtain a phase-inverted membrane.

16. The process of claim 15, further including leaching of the phase-inverted membrane.

17. The process of claim 14, wherein said free radical polymerizable monomer is positively charged.

18. The process of claim 17, wherein said positively charged monomer is an acrylic monomer containing a quaternary ammonium group.

19. The process of claim 14, wherein said free radical polymerizable monomer is negatively charged.

20. The process of claim 19, wherein said negatively charged free radical polymerizable monomer contains a sulfonic acid group.

21. The hydrophilic charged microporous membrane produced by the process of claim 14.

22. The process of claim 14, wherein said polyacrylate is a diacrylate.

23. The process of claim 22, wherein said diacrylate is an alkyleneglycol diacrylate.

24. The process of claim 14, wherein said polymer of said matrix is selected from the group consisting of polyaromatics, polysulfones, polyolefins, polystyrenes, polyamides, polyimides, fluoropolymers, polycarbonates, polyesters, and cellulose acetates.

* * * * *

UNITED STATES PATENT AND TRADEMARK OFFICE
CERTIFICATE OF CORRECTION

PATENT NO.    : 6,849,185 B1
DATED         : February 1, 2005
INVENTOR(S)   : Wu et al.

It is certified that error appears in the above-identified patent and that said Letters Patent is hereby corrected as shown below:

Title page,
Item [60], Related U.S. Application Data, Provisional application No. 60/134,197, filed May 14, "1997" should read -- 1999 --.

Signed and Sealed this

Thirty-first Day of January, 2006

JON W. DUDAS
*Director of the United States Patent and Trademark Office*

UNITED STATES PATENT AND TRADEMARK OFFICE
CERTIFICATE OF CORRECTION

PATENT NO.      : 6,849,185 B1
APPLICATION NO. : 09/959882
DATED           : February 1, 2005
INVENTOR(S)     : Wu et al.

It is certified that error appears in the above-identified patent and that said Letters Patent is hereby corrected as shown below:

Title Page, item [73] Assignee: should read as follows:

PALL CORPORATION
2200 Northern Boulevard
East Hills, NY 11548-1209

Signed and Sealed this

Fourteenth Day of April, 2009

JOHN DOLL
*Acting Director of the United States Patent and Trademark Office*